US009862919B2

(12) United States Patent
Niedl et al.

(10) Patent No.: US 9,862,919 B2
(45) Date of Patent: Jan. 9, 2018

(54) DEVICE AND METHOD FOR IDENTIFICATION OF MICROORGANISMS

(71) Applicant: DIAMOND INVENTION UG (HAFTUNGSBESCHRAENKT), Schwielowsee (DE)

(72) Inventors: Robert Niedl, Berlin (DE); Carsten Beta, Berlin (DE)

(73) Assignee: DIAMOND INVENTION UG (HAFTUNGSBESCHRAENKT), Schwielowsee (DE)

( * ) Notice: Subject to any disclaimer, the term of this patent is extended or adjusted under 35 U.S.C. 154(b) by 0 days.

(21) Appl. No.: 14/931,917

(22) Filed: Nov. 4, 2015

(65) Prior Publication Data
US 2016/0160166 A1  Jun. 9, 2016

(30) Foreign Application Priority Data
Nov. 4, 2014 (DE) ........................ 10 2014 116 050

(51) Int. Cl.
C12M 1/34 (2006.01)
C12M 1/00 (2006.01)
C12M 1/30 (2006.01)
C12Q 1/04 (2006.01)
B01L 9/00 (2006.01)
B01L 3/00 (2006.01)
G01N 21/84 (2006.01)
(Continued)

(52) U.S. Cl.
CPC ........... *C12M 23/20* (2013.01); *B01L 3/5023* (2013.01); *B01L 9/52* (2013.01); *C12M 23/38* (2013.01); *C12M 25/02* (2013.01); *C12M 33/02* (2013.01); *C12M 37/04* (2013.01); *C12Q 1/04* (2013.01); *G01N 21/8483* (2013.01); *B01L 2200/0621* (2013.01); *B01L 2300/047* (2013.01); *B01L 2300/0816* (2013.01); *B01L 2300/0851* (2013.01); *B01L 2300/0887* (2013.01); *B01L 2300/126* (2013.01); *B01L 2400/0406* (2013.01); *C12Q 1/689* (2013.01)

(58) Field of Classification Search
CPC .................................................... C12M 33/14
See application file for complete search history.

(56) References Cited

FOREIGN PATENT DOCUMENTS

| WO | 2004048936 A2 | 6/2004 |
| WO | 2006113930 A2 | 10/2006 |
| WO | 2012092242 A2 | 7/2012 |

*Primary Examiner* — Rosanne Kosson
(74) *Attorney, Agent, or Firm* — JMB Davis Ben-David

(57) ABSTRACT

The present invention relates to a device for the identification of microorganisms, comprising:
a) a carrier 1, wherein an absorbent material 2 is arranged on the carrier 1,
b) at least one intermediate sealing layer 3, with at least one cut-out 4, which is designed to receive the microorganisms to be identified, these being present on a micropore filter 5,
c) at least one nonwoven reaction fabric comprising an absorbent material 2 on which at least one absorption field 7 and/or at least one liquid-transporting structure 8 is arranged for the taking up of reagents to identify microorganisms, and
d) a cover plate 9.
Furthermore, a method for the identification of microorganisms is used in conjunction with the device according to the invention.
With the present invention, microorganisms in a sample can be identified very quickly—within a few minutes. In this, the test system is isolated from the environment, so avoiding danger to people and the environment from a positive test finding.

13 Claims, 3 Drawing Sheets

(51) Int. Cl.
*C12M 1/12* (2006.01)
*C12Q 1/68* (2006.01)

DEVICE AND METHOD FOR IDENTIFICATION OF MICROORGANISMS

CROSS-REFERENCE TO RELATED APPLICATIONS

The present application claims priority under 35 U.S.C. 119(a)-(d) to the following foreign application, which is incorporated herein by reference: German Application No. 10 2014 116 050.9, filed Nov. 4, 2014.

BACKGROUND OF THE INVENTION

This invention relates to a device and a method for the identification of microorganisms.

With changes in the drinking water ordinance (TrinkwV2001), it was laid down that hot water storage systems with a storage capacity of more than 200 liters and hot drinking water piping systems with a volume of more than 3 liters must be regularly investigated for bacteria such as the microorganisms *Legionella* or *E. coli*. In addition, respiratory systems such as mobile respiration machines, oxygen or respiratory air lines in hospitals etc. must be regularly checked and maintained.

Up to now these tests have been performed via diagnostic analysis in the laboratory on previously taken sample solutions or filter devices. Special microbiological culture mediums with test smears have been provided and examined after appropriate incubation periods under optimum conditions for the target organisms. These test methods described have up to now taken several days, even weeks, so that the corresponding systems with findings are still in operation during the test period, or previously systems tested as positive have not been released for the analysis period although a germ contamination no longer exists.

SUMMARY OF THE INVENTION

The object of the present invention is therefore to overcome the disadvantages of the state of the art.

The object of the invention is to provide a device for the identification of microorganisms. The identification of microorganisms by means of this device takes place in a few minutes. In this, the sensitivity must be at least the same as that of well-known systems known in the art and keep to the legally accepted methods of analysis.

Furthermore, it is the object of the invention to provide a device that is isolated from the environment to avoid danger to people and the environment in the case of a positive finding.

It is also an object of the invention to provide a device that makes a disposable, one-off application possible.

The object of the present invention is achieved by providing a device for the identification of microorganisms which has the features of the main claim. Advantageous modifications of the device according to the invention are featured in the dependent subclaims.

Object of the invention is a device for the identification of microorganisms comprising:
a) a carrier wherein an absorbent material is arranged on the carrier,
b) at least one intermediate sealing layer, with at least one cut-out, which is designed to receive the microorganisms to be identified, these being present on a micropore filter,
c) at least one nonwoven reaction fabric comprising an absorbent material on which at least one absorption field and/or at least one liquid-transporting structure is arranged for the taking up of reagents to identify microorganisms, and
d) a cover plate.

According to the invention, a device is preferred in which the carrier and/or cover plate is made of glass, polyethylene, polypropylene, polyvinyl chloride, polystyrene, cyclic olefin copolymers, polymethyl methacrylate or polyurethane.

Especially preferred is a device according to the invention in which the absorbent material is made from paper, cellulose-based substrates, polyethylene, polyether sulfone or polycarbonate.

Especially preferred is a device according to the invention in which the intermediate sealing layer is made from a liquid-impermeable material.

A device according to the invention is also preferred in which the intermediate layer is firmly glued to or pressed together with the absorbent material.

Furthermore, a device according to the invention is preferred with which more than one nonwoven reaction fabric and more than one intermediate sealing layer is provided, wherein the nonwoven reaction fabric and the intermediate sealing layer are arranged alternately.

Especially preferred is a device according to the invention in which a switchable storage reservoir is arranged on at least one absorption field.

Preferred is a device according to the invention in which the at least one storage reservoir is connected to a liquid-transporting structure.

Especially preferred is a device according to the invention in which the switchable storage reservoir is a polymer gel.

Especially preferred is a device in which a solvent and/or reagent is inserted into the storage reservoir.

Further preferred is a device according to the invention in which at least one take-up facility is arranged within the at least one absorption field and/or the at least one liquid-transporting structure into which at least one solvent and/or reagent is placed.

A device according to the invention is also preferred in which at least one solvent and/or reagent can be applied directly from outside and/or by means of a stimulus applied to the at least one storage reservoir onto the absorption field and/or at least one liquid-transporting structure.

The object of the present invention is further achieved by a method for the identification of microorganisms using the device according to the invention.

The object of the present invention is achieved by a method for the identification of microorganisms using the device according to the invention, wherein
a) a micropore filter is charged with a sample,
b) the micropore filter is arranged in a cut-out, on a cut-out or under a cut-out of an intermediate layer,
c) at least one solvent and/or reagent is brought into at least one take-up facility of the at least one absorption field and/or in at least one liquid-transporting structure and/or in at least one storage reservoir,
d) the storage reservoir of c) is arranged on an absorption field,
e) the constituent parts of the device are assembled according to claim 1,
f) at least one stimulus is generated at at least one storage reservoir or a solvent and/or reagent is applied directly from the outside onto the absorbent material of the nonwoven reaction fabric and
g) the microorganisms contained in the sample of a) are identified.

A method according to the invention is preferred, wherein at least one reagent in c) is present in a dried form.

A method according to the invention is especially preferred, wherein at least one solvent or reagent in d) exists in a solidified form.

Especially preferred is a method according to the invention, wherein the stimulus in f) is thermal radiation, a change in pH value, UV radiation or electrical stimulus.

A method according to the invention is also especially preferred, wherein the stimulus triggers the liquefaction of the solvent or reagent which is arranged on and/or in the absorption field.

A further method according to the invention is preferred wherein in g) the microorganisms can be identified on the basis of a color change.

In the context of the present invention, solvents and/or reagents can be selected for microorganism-specific antibodies, which are marked with an enzyme, enzymes, redox dyes, water, alcohols, diluted acids, bases, proton donators or acceptors.

Furthermore, in the context of the present invention, liquid transporting structures can be selected from channels, tubes or wettable fiber networks, which preferably have a geometry of the order $10^{-3}$ to $10^{-6}$ m.

In addition, in the context of the present invention, are storage reservoirs made from hydrogels or polymer gels, which can store water or dilute acids and can be released again by a change in external energy, preferably light, pH value or temperature stimuli.

Furthermore in the context of the present invention, liquid-impermeable material is selected from double-sided adhesive film, latex, silicone, paraffin, a layer of glue or a lacquer coating.

BRIEF DESCRIPTION OF THE DRAWINGS

The present invention is explained in more detail by means of the accompanying drawings. They show in.

DETAILED DESCRIPTION OF THE INVENTION

The known test methods for identification of microorganisms have up to now taken several days, even weeks, so that the corresponding systems with findings are still in operation during the test period, or previously systems tested as positive have not been released for the analysis period although a germ contamination no longer exists.

The present invention discloses a device and method by which this test period for identification of microorganisms can be reduced to that of a quick-test system lasting a few minutes. In this it is advantageous, that this procedure exhibits at least the same sensitivity as that of the prior, established and legally accepted analysis methods.

Furthermore, it is advantageous that the quantity of medium or gas to be investigated in which the microorganisms to be identified are located, can be freely varied without having to change the device and/or the method.

A further advantage of the device according to the invention is the use of paper, cellulose-based substrates, polyethylene, polyether sulfone or polycarbonate as absorbent material. The use of inexpensive materials has a positive effect on the manufacturing costs of the device according to the invention. The device according to the invention is therefore conceived as a disposable quick-test system.

Because the constituent components of the device according to the invention are firmly sealed together, the device is isolated from the environment in the case of a positive microorganism finding, so that a de facto danger to people and environment from the test system can be excluded.

According to the invention, a specific antibody test can be utilized to determine the microorganisms. Because of that, it is then advantageous that the object of the present invention can be quickly adapted to any number of identified microorganisms—in so far as an adequately specific antibody exists.

The following examples explain, together with reference to the figures, the invention in more detail without restricting the scope of the invention.

Figure 1:
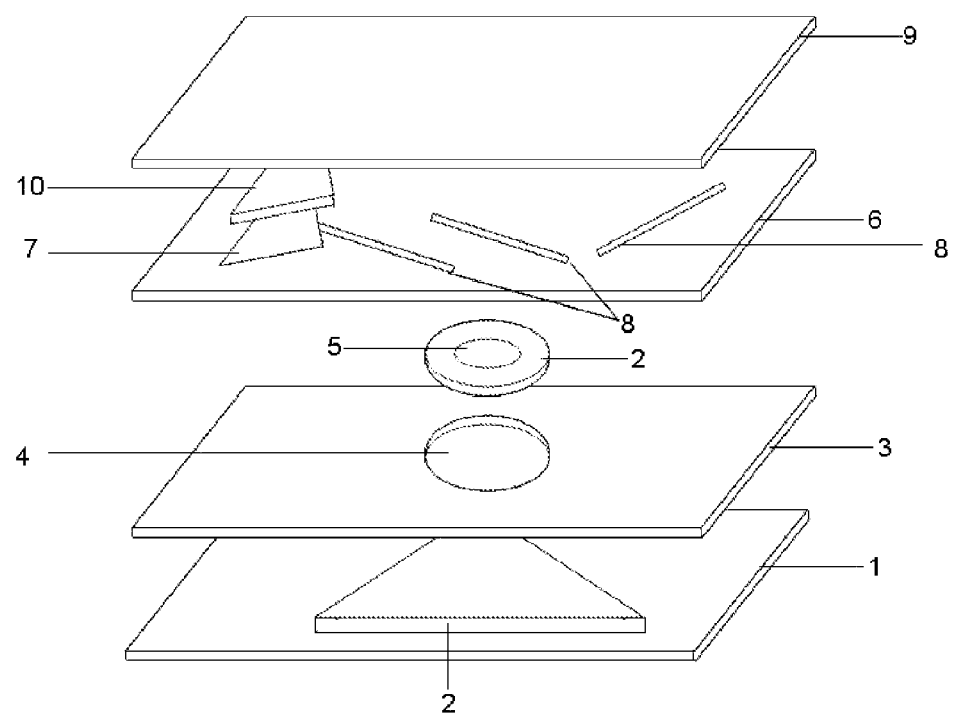
FIG. 1 a schematic representation of the structure of a first embodiment of the device according to the invention, FIG. 2 a schematic representation of a second embodiment of the device according to the invention, and FIG. 3 a schematic representation of a third embodiment of the device according to the invention.

In FIG. 1, there is shown a first preferred embodiment of the device according to the invention for identifying microorganisms. The device according to the invention comprises a carrier 1 on which an absorbent material 2, paper for example, is fixed. The absorbent material 2 on carrier 1 can function as end reservoir, which catches through-flowing liquids. An intermediate layer 3 of liquid-impermeable material is arranged on the absorbent material 2. A cutout 4 is made within the intermediate layer 3, into which a micropore filter 5 with the microorganisms to be identified, is to be inserted. According to the invention, the micropore filter 5 can the laid on an absorbent material 2. The absorbent material 2 serves for example as a bridge in order to compensate for the difference in height between the absorbent material 2 on the carrier 1 and the surface of the intermediate layer 3. The micropore filter 5 can however also be arranged directly underneath the cut-out 4 arranged on the absorbent material 2 that is fixed to carrier 1.

A nonwoven reaction fabric 6 made from an absorbent material 2 is arranged above the intermediate layer 3. An absorption field 7 and three liquid-transporting structures 8, formed as channels, are arranged in the nonwoven reaction fabric 6. According to the invention, it is possible for only absorption fields 7 or only liquid-transporting structures 8 to be arranged in the nonwoven reaction fabric 6, wherein the number thereof is variable in the respective case. The individual channels then represent, with the intermediate layers and the nonwoven reaction fabric s, an interconnected channel system over several layers.

A storage reservoir 10 is arranged on the absorption field 7 wherein the storage reservoir 10 can be a hydrogel or a polymer gel. Furthermore, take-up facilities are provided in the liquid-transporting structures 8 that, according to the invention, can absorb the liquid or dried reagents and/or solvents. In addition, solvents and/or reagents can also be inserted on to the absorption fields 7 and into the storage reservoirs 10.

A cover plate 9 is arranged above the nonwoven reaction fabric 6. The device according to the invention, when assembled, is a closed, airtight system isolated from the environment. This prevents hazards to people and the environment if a finding is positive. A further advantage according to the invention is the use of inexpensive materials, so reducing manufacturing costs. In addition, the device according to the invention represents a disposable quick-test system, which can be disposed of after use. There are therefore no waiting times following a positive finding within a system until the system can be used again.

Figure 2:
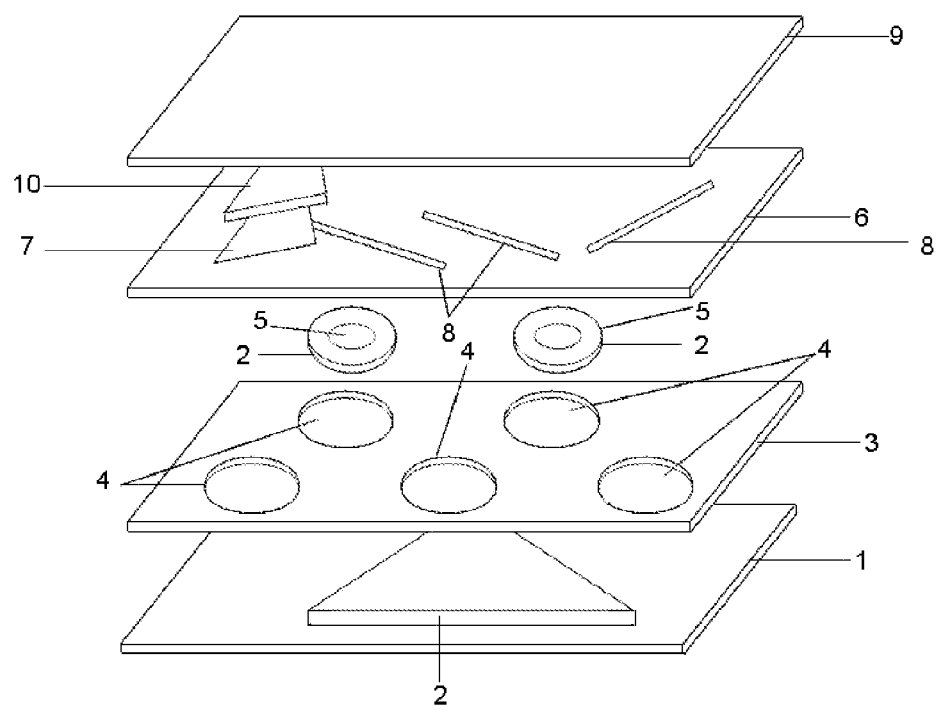

In FIG. 2, there is shown a second embodiment of the device according to the invention. In this embodiment, which is also preferred, there is a difference between it and the embodiment in FIG. 1 in that a plurality of cut outs 4 are arranged within the intermediate layer 3. According to the invention, a plurality of various microorganisms on different micropore filters 5 of the same or different samples can be identified. Advantageous there is the simultaneous procedure of identifying the microorganisms of various samples, so leading to an enormous reduction in the time required. In addition, only a device according to the invention with the appropriately necessary materials is used, which has a positive effect on the manufacturing costs.

Figure 3:
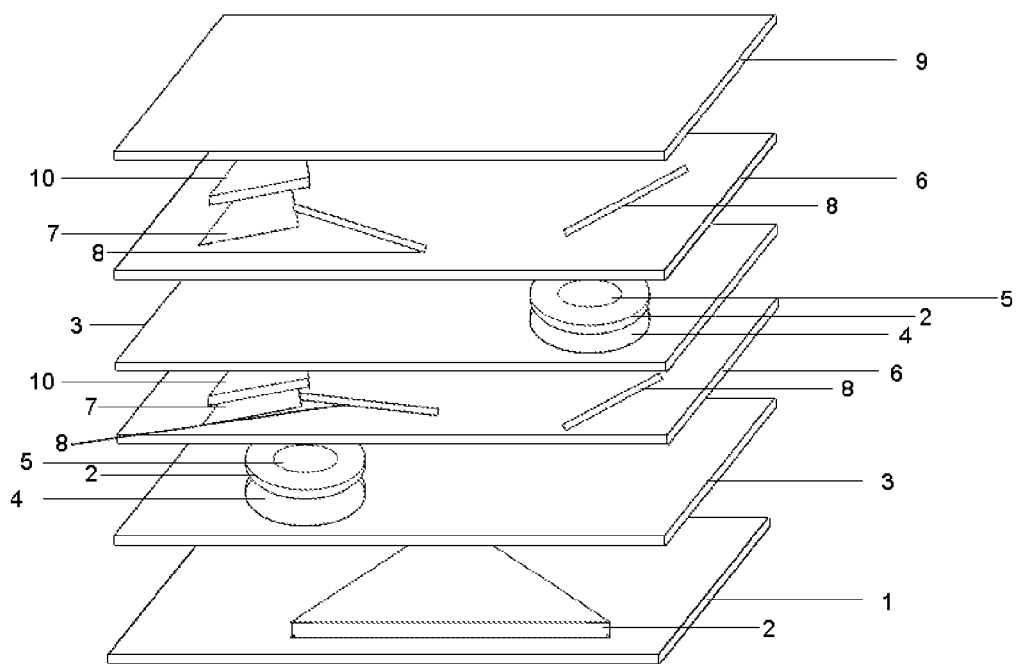

In FIG. 3, there is shown a third advantageous preferred embodiment of the device according to the invention. In this embodiment, the device according to the invention includes a second intermediate layer 3 and a second nonwoven reaction fabric 6 compared with the embodiment in FIG. 1. Within the device according to the invention, the intermediate layer 3 and the nonwoven reaction fabric 6 are arranged alternately, wherein the total number of alternating layers is variable. With this, a plurality of analytic reactions of a sample can advantageously run in parallel to one another within a device according to the invention. For example, one reaction can represent a detection reaction for the identification of the microorganisms on a micropore filter 5 and the other reaction to be proof of whether the microorganisms to be identified on a second micropore filter 5 are still alive.

The following embodiment examples describe in more detail the method according to the invention using the device according to the invention, without restricting the scope of the invention.

EXAMPLE 1

Because of the necessary safety restrictions S2 for pathogenic microorganisms (here *Legionellae*), the device according to the invention and the method according to the invention were tested with *E. coli*. By the use of a specific antibody against an alternative microorganism, for example *Legionella* spec., *Salmonella* spec., the test system can however be extended to any other microorganism.

Firstly, the device according to the invention is prepared. To do this, a specific antibody marked with peroxidase is dry-stored upstream in a first take-up facility in a linear channel inside the nonwoven reaction fabric . The nonwoven reaction fabric is made from a channel-structured paper, for example, as an absorbent material. In a second take-up facility of the forked channel, a redox dye—for example tetramethylbenzidine—is stored upstream in the dry state. In the same channel, a peroxide is dry-stored upstream as proton donor in a third take-up facility.

A storage reservoir in the form of a water-storing hydrogel is then applied to a first absorption field. A hydrogel is applied to a second absorption field in which a dilute sulfuric acid exists in stored form.

The cover plate used to tightly seal the device according to the invention from above. An end reservoir is fixed from an absorbent material onto the carrier with the help of an intermediate layer made from double-sided adhesive film. In the middle of the double-sided adhesive film, a cut-out is made which is filled by a connecting bridge made from absorbent material. The so prepared device according to the invention is now ready for use.

A micropore filter is connected to the gas or liquid transport system with the help of a commonplace holding device. A pre-defined target volumetric quantity of medium is then transported through the micropore filter.

The holding device is then loosened from the system to be tested and the micropore filter removed. The side of the micropore filter facing the incoming flow is defined as the upper side. The filter side in the flow direction is defined as the lower side.

The micropore filter that has been removed is now glued inside the cut-out of the intermediate layer with the lower side located on the middle of the connecting bridge which is made of absorbent material. The carrier with the centered cover plate is then pressed on by hand so that the device according to the invention is closed and airtight.

A thermal stimulus, here 38° C. for example, is used to collapse the hydrogel on the first absorption field, so releasing the water stored there. The capillary forces of the absorbent material pull the water into the first take-up facility of the linear channel where it dissolves the antibody previously stored there. Subsequently, the water is drawn through the micropore filter to the end reservoir. In the micropore filter, a part of the antibody is specifically bound to the microorganisms located there for identification.

In a second step, the hydrogel that is arranged on the second absorption field, is also thermally collapsed at 38° C. This releases the dilute sulfuric acid. This is also drawn through the absorbent material and into the channel by capillary forces where it dissolves the peroxide and reacts with this at a third take-up facility. The reaction product is drawn to a second take-up facility and soaks there the absorbent material containing the tetramethylbenzidine. Here, the already soaked micropore filter and the tetramethylbenzidine come into contact. The microorganisms, previously marked with the specific antibody, react, with the help of the peroxidase attached to the antibody, with the redox dye. Due to the reaction, a color change becomes visible, from yellow/green to blue in the present example of an embodiment.

Because of the speed of the color change, the user can read off the positive finding of the microorganisms to be identified in the present invention.

As an alternative, the method according to the invention can also be photometrically automated and/or run with the help of electrodes made of conducting materials previously inserted in the system. In this case, the finding is read out electrochemically and therefore subsequently evaluated electronically.

Advantageous in the present invention is the combination of micropore filters with defined pore size and increase in concentration of the microorganisms to be identified using, for example, a paper-based microfluid quick-test system with redox dye-based antibody test. Also positive is the use of responsive hydrogel, wherein the present invention can be performed completely automatically and is therefore free from user errors. In addition, an advantage of the present invention is that this can also be operated if required without the use of hydrogels or polymer gels, wherein the solutions can then be fed in from outside the system.

EXAMPLE 2

In a second embodiment of the present invention, the device according to the invention and the method according to the invention are basically built up and carried out, as already described in Example 1. In contrast to the first embodiment, the preparation of the device according to the invention has however two intermediate layers and two nonwoven reaction fabric arranged alternately between the carrier and the cover plate.

According to the invention, such a structure serves on the one hand to identify the organisms present on the micropore filter and, on the other hand, to analyze whether the microorganisms in the sample to be investigated are still alive. This can be achieved by a color test of metabolic products, for example adenosine triphosphate (ATP).

Initially, the first nonwoven reaction fabric is appropriately prepared, as already described in Example 1, and an intermediate layer with the cut-out for a micropore filter arranged under the nonwoven reaction fabric.

A second nonwoven reaction fabric similar to the first nonwoven reaction fabric is then prepared, wherein various reagents and/or solvents in hydrogels are applied to the absorption fields, and/or in the appropriate take-up facilities of the liquid-transporting structures in a liquid, solid and/or dried state. This setup can be used to perform a test on the microorganisms to show whether they are alive. The reagents and/or solvents required for this are known to the skilled artesian.

The same test as described in Example 1 is then carried out, wherein two micropore filters are used to take the samples from a gas-transporting or liquid-transporting system.

After that, the one micropore filter is arranged in a cut-out of the first intermediate layer and the other micropore filter in a cut-out of the second intermediate layer.

Advantageous in this embodiment example is that the different analyses of the microorganisms, the identification and the "alive" test can take place in the same device according to the invention. This has a positive effect on the manufacturing costs and the time spent. In this, it is also advantageous that the liquid volumes, in the hydrogels for example, can be set individually. It is therefore possible to set the volume in such a way that a soaking of the second nonwoven reaction fabric with the liquid from the first nonwoven reaction fabric is avoided. It is also advantageous in the invention-related embodiment that even a soaking of the second nonwoven reaction fabric would not lead to a false statement as different reagents and/or solvents are used in the first and second nonwoven reaction fabric.

LIST OF REFERENCE NUMBERS

1 Carrier
2 Absorbent material
3 Intermediate sealing layer
4 Cut-out
5 Micropore filter
6 Nonwoven reaction fabric
7 Absorption field
8 Liquid-transporting structure
9 Cover plate
10 Storage reservoir

The invention claimed is:

1. A device for the identification of microorganisms comprising:
   a) a carrier, wherein an absorbent material is arranged on the carrier,
   b) at least one intermediate sealing layer, with at least one cut-out, which is designed to receive the microorganisms to be identified, said microorganisms being present on a micropore filter,
   c) at least one nonwoven reaction fabric comprising one absorbent material, on which at least one absorption field and at least one liquid-transporting structure for the taking up of reagents to identify the microorganism are arranged and
   d) a cover plate.

2. The device according to claim 1, wherein the carrier and/or the cover plate are made of glass, polyethylene, polypropylene, polyvinyl chloride, polystyrene, cyclic olefin copolymers, polymethyl methacrylate or polyurethane.

3. The device according to claim 1, wherein the absorbent material is made from paper, cellulose-based substrates, polyethylene, polyether sulfone or polycarbonate.

4. The device according to claim 1, wherein the intermediate sealing layer is made from a liquid-impermeable material.

5. The device according to claim 4, wherein the intermediate sealing layer is pressed firmly together with, or glued to, the absorbent material.

6. The device according to claim 1, wherein more than one nonwoven reaction fabric and more than one intermediate sealing layer are provided, and wherein the nonwoven reaction fabric and the intermediate sealing layer are arranged alternately.

7. The device according to claim 1, further comprising at least one switchable storage reservoir arranged on the at least one absorption field.

8. The device according to claim 7, wherein the at least one storage reservoir is connected to a liquid-transporting structure.

9. The device according to claim 7, wherein the switchable storage reservoir is a polymer gel.

10. The device according to claim 7, wherein a solvent and/or reagent is inserted within the storage reservoir.

11. The device according to claim 1, wherein, within the at least one absorption field and/or the at least one liquid-transporting structure, at least one absorptive structure that can absorb a liquid reagent and/or solvent is arranged into which the solvent and/or liquid reagent is placed.

12. The device according to claim 1, wherein at least one solvent and/or reagent can be applied directly from outside and/or by a stimulus applied to the at least one storage reservoir onto the absorption field and/or the at least one liquid-transporting structure.

13. A method for the identification of microorganisms using the device according to claim 1, comprising the steps of
   a) placing a sample comprising microorganisms in the micropore filter,
   b) placing at least one solvent and/or liquid reagent in the absorption field and/or liquid-transporting structure and/or in one storage reservoir, so that the solvent and/or liquid reagent flows into micropore filter,
   c) effecting a detectable reaction between the solvent and/or the liquid reagent and the microorganisms that allows for identification of the microorganisms and
   g) identifying the microorganisms contained in the sample in the micropore filter.

* * * * *